US012569745B2

(12) United States Patent
Shimizu

(10) Patent No.: US 12,569,745 B2
(45) Date of Patent: Mar. 10, 2026

---

(54) HEART RATE CONTROL DEVICE

(71) Applicant: CITIZEN WATCH CO., LTD., Tokyo (JP)

(72) Inventor: Hideki Shimizu, Saitama (JP)

(73) Assignee: CITIZEN WATCH CO., LTD., Tokyo (JP)

(*) Notice: Subject to any disclaimer, the term of this patent is extended or adjusted under 35 U.S.C. 154(b) by 989 days.

(21) Appl. No.: 16/978,375

(22) PCT Filed: Feb. 21, 2019

(86) PCT No.: PCT/JP2019/006634
§ 371 (c)(1),
(2) Date: Sep. 4, 2020

(87) PCT Pub. No.: WO2019/171975
PCT Pub. Date: Sep. 12, 2019

(65) Prior Publication Data
US 2020/0406000 A1 Dec. 31, 2020

(30) Foreign Application Priority Data

Mar. 8, 2018 (JP) ................................. 2018-041845

(51) Int. Cl.
A63B 71/06 (2006.01)
A61B 5/00 (2006.01)
(Continued)

(52) U.S. Cl.
CPC .......... A63B 71/0686 (2013.01); A61B 5/486 (2013.01); A61M 21/02 (2013.01);
(Continued)

(58) Field of Classification Search
CPC .......... A63B 71/0686; A63B 2230/067; A63B 2071/0688; A61B 5/486; A61B 5/024;
(Continued)

(56) References Cited

U.S. PATENT DOCUMENTS

2006/0253161 A1 11/2006 Libbus et al.
2008/0027516 A1* 1/2008 Wu ..................... A61M 16/161
607/88

(Continued)

FOREIGN PATENT DOCUMENTS

CN 103415319 A 11/2013
CN 103547240 A 1/2014
(Continued)

OTHER PUBLICATIONS

M. A. Schwarz, I. Winkler, and P. Sedlmeier, "The Heart Beat Does not Make us Tick: The impacts of heart rate and arousal on time perception," Attention, Perception, &amp; Psychophysics, vol. 75, No. 1, pp. 182-193, 2012 (Year: 2012).*
(Continued)

*Primary Examiner* — Amanda L Steinberg
(74) *Attorney, Agent, or Firm* — Imaizumi IP Law, PLLC; Toshikatsu Imaizumi

(57) ABSTRACT

Provided is a heart-rate control device capable of adjusting the heart rate of a subject to a desired value between a base heart rate and an active heart rate, such as a heart rate immediately after physical exercise. The heart-rate control device includes a detector for detecting heartbeat information of a subject, an input unit to which information on a target value relating to a heart rate of the subject is to be inputted, a difference extracting unit for determining a difference between the target value and a current value relating to the heart rate of the subject, the current value being calculated from the heartbeat information, a pattern generating unit for generating a stimulus pattern depending on the difference so that the current value approaches the target value, the stimulus pattern being a combination of a sympathetic nerve stimulus for stimulating sympathetic nerves, a parasympathetic nerve stimulus for stimulating parasympathetic nerves, and an initialization stimulus for
(Continued)

preventing stimulus saturation of the sympathetic nerves or the parasympathetic nerves, and an output unit for outputting the sympathetic nerve stimulus, the parasympathetic nerve stimulus and the initialization stimulus to the subject in accordance with the stimulus pattern.

10 Claims, 11 Drawing Sheets

(51) Int. Cl.

| | |
|---|---|
| A61B 5/024 | (2006.01) |
| A61M 21/00 | (2006.01) |
| A61M 21/02 | (2006.01) |
| A61N 1/362 | (2006.01) |

(52) U.S. Cl.
CPC ........... *A61N 1/3625* (2013.01); *A61B 5/024* (2013.01); *A61M 2021/0027* (2013.01); *A61M 2021/0044* (2013.01); *A61M 2021/0066* (2013.01); *A61M 2230/06* (2013.01); *A63B 2071/0688* (2013.01); *A63B 2230/067* (2013.01)

(58) Field of Classification Search
CPC .......... A61M 21/02; A61M 2021/0027; A61M 2021/0044; A61M 2021/0066; A61M 2230/06; A61N 1/3625
See application file for complete search history.

(56) References Cited

U.S. PATENT DOCUMENTS

| | | | |
|---|---|---|---|
| 2009/0248119 A1 | 10/2009 | Libbus et al. | |
| 2010/0169409 A1* | 7/2010 | Fallon .................... | G16H 10/60 |
| | | | 707/802 |
| 2011/0034782 A1 | 2/2011 | Hamann | |
| 2012/0022608 A1 | 1/2012 | Libbus et al. | |
| 2012/0095534 A1* | 4/2012 | Schlangen ............ | A61M 21/00 |
| | | | 607/90 |
| 2012/0206050 A1* | 8/2012 | Spero ................... | H05B 45/395 |
| | | | 315/152 |
| 2012/0296395 A1 | 11/2012 | Hamann | |
| 2013/0211471 A1 | 8/2013 | Libbus et al. | |
| 2014/0194952 A1 | 7/2014 | Libbus et al. | |
| 2015/0294574 A1* | 10/2015 | Pacione .............. | A61B 5/7246 |
| | | | 434/236 |
| 2016/0346501 A1* | 12/2016 | Hooper ................ | A61B 5/4836 |
| 2017/0079598 A1* | 3/2017 | Stolen .................... | A61B 5/318 |
| 2018/0042486 A1* | 2/2018 | Yoshizawa ......... | A61B 5/02125 |
| 2018/0050207 A1 | 2/2018 | Hamann | |
| 2019/0001129 A1* | 1/2019 | Rosenbluth .............. | A61N 1/08 |

FOREIGN PATENT DOCUMENTS

| | | | | |
|---|---|---|---|---|
| JP | H11-135273 A | | | 5/1990 |
| JP | 2000-70373 A | | | 3/2000 |
| JP | 2000-294387 A | | | 10/2000 |
| JP | 2001-252265 A | | | 9/2001 |
| JP | 2004222818 A | * | | 8/2004 |
| JP | 2008125802 A | * | | 6/2008 |
| JP | 2008-539961 A | | | 11/2008 |
| JP | 2009-283317 A | | | 12/2009 |
| JP | 2012-120640 A | | | 6/2012 |
| JP | 2014-516692 A | | | 7/2014 |
| WO | 2006/122148 A2 | | | 11/2006 |
| WO | 2007/063900 A1 | | | 6/2007 |
| WO | 2012/092364 A2 | | | 7/2012 |
| WO | 2012/158766 A1 | | | 11/2012 |
| WO | 2012/173634 A1 | | | 12/2012 |

OTHER PUBLICATIONS

China National Intellectual Property Administration, First Office Action for Chinese Patent Application No. 201980017584.4, Feb. 28, 2022.
WIPO, International Search Report for International Patent Application No. PCT/JP2019/006634, May 14, 2019.
WIPO, Written Opinion for International Patent Application No. PCT/JP2019/006634, May 14, 2019.

\* cited by examiner

FIG. 9
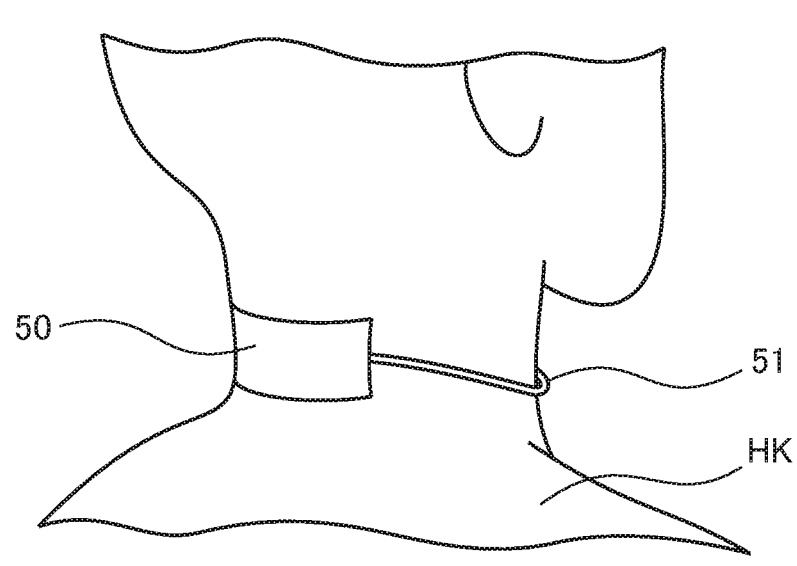
FIG. 10 (A)                    FIG. 10 (B)
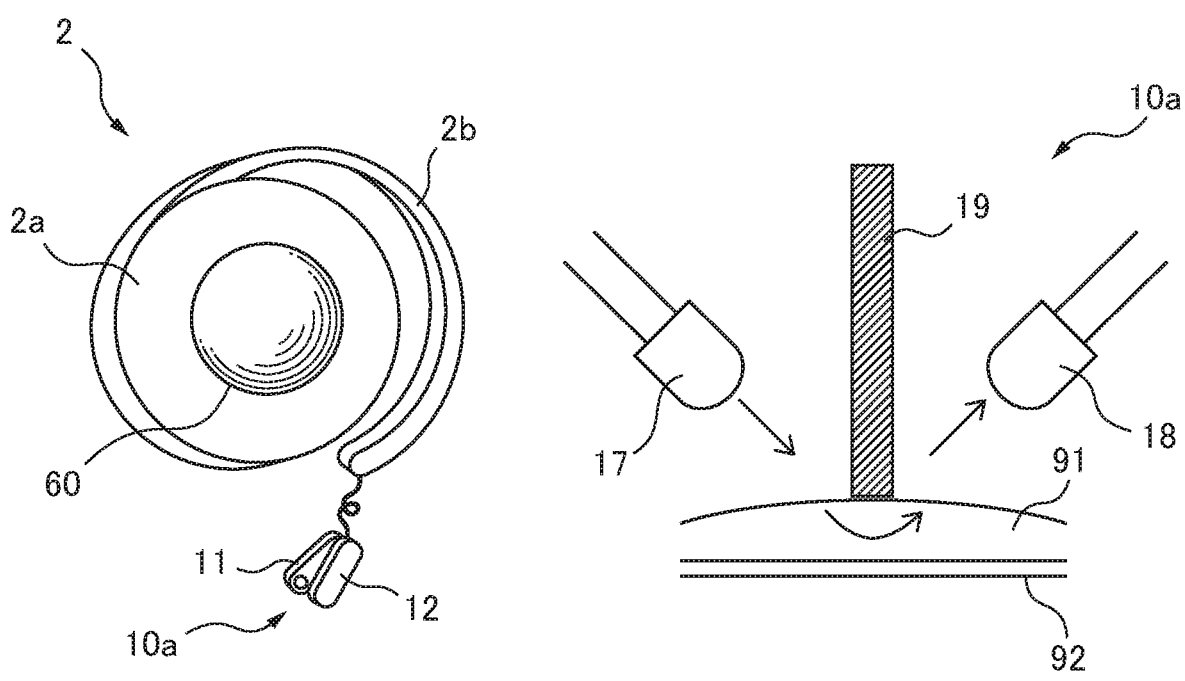

HEART RATE CONTROL DEVICE

FIELD

The present invention relates to a heart-rate control device.

BACKGROUND

Biofeedback apparatuses and lighting apparatuses have been proposed that sense a heartbeat of a user, estimate his/her current mental state and feed information for stimulating the senses of sight and hearing back to the user so that the current mental state may approach a target mental state. For example, Patent Literature 1 describes a biofeedback apparatus that detects biomedical reactions of a user, judges mental activities of the user on the basis of the results of the detection, and provides time-varying stimuli to the five senses of the user, depending on the results of the judgment. Patent Literature 2 describes a method of controlling a lighting apparatus so as to emit mainly low color temperature light during a quiescent period in a human biorhythm and emit mainly high color temperature light during an active period in the human biorhythm. The above apparatus and method provide stimuli to the five senses of the user, and thereby stimulate sympathetic nerves so that the mental state approaches an active state in which the heart rate increases, or stimulate parasympathetic nerves so that the mental state approaches a resting state in which the heart rate decreases.

Patent Literature 3 describes a neural stimulation system that senses autonomic activities and applies neural stimulation to sympathetic and parasympathetic nerves to control autonomic balance. Patent Literature 4 describes an illuminating apparatus emitting light whose color does not increase the heart rate during a warm-up time from the start of exercise, light whose color increases the heart rate to improve the effect of the exercise during a main exercise time after the warm-up time, and again light whose color decreases the heart rate during a cooldown time after the main exercise time. Patent Literature 5 describes a color-temperature control lighting system that alternately emits low color temperature light having a relaxing effect and intermediate color temperature light and that alternately emits high color temperature light having an awaking effect and intermediate color temperature light, wherein the period of these alternations is shorter than a time interval required for chromatic adaptation of a human.

CITATION LIST

Patent Literature

Patent Literature 1: Japanese Unexamined Patent Publication No. JP 2001-252265
Patent Literature 2: Japanese Unexamined Patent Publication No. JP 2000-294387
Patent Literature 3: Japanese Unexamined Patent Publication No. JP 2008-539961
Patent Literature 4: Japanese Unexamined Patent Publication No. JP 2009-283317
Patent Literature 5: Japanese Unexamined Patent Publication No. JP H11-135273

SUMMARY

It is known that there is a correlation between heart rates and metabolism of a human and that the metabolism increases as the heart rate increases. If color and auditory stimuli are provided to sympathetic and parasympathetic nerves, as in, for example, the biofeedback apparatus of Patent Literature 1, the heart rate of the user (subject) of the apparatus will vary toward a target value. However, if stimuli are simply provided, the sympathetic and parasympathetic nerves will adapt thereto with the passage of time, and the heart rate of the subject will vary only slightly and then be saturated, and therefore cannot be necessarily adjusted to a desired value.

Accordingly, it is an object of the present invention to provide a heart-rate control device capable of adjusting the heart rate of a subject to a desired value between a base heart rate and an active heart rate, such as a heart rate immediately after physical exercise.

Provided is a heart-rate control device including a detector for detecting heartbeat information of a subject, an input unit to which information on a target value relating to a heart rate of the subject is to be inputted, a difference extracting unit for extracting a difference between the target value and a current value relating to the heart rate of the subject, the current value being calculated from the heartbeat information, a pattern generating unit for generating a stimulus pattern depending on the difference so that the current value approaches the target value, the stimulus pattern being a combination of a sympathetic nerve stimulus for stimulating sympathetic nerves, a parasympathetic nerve stimulus for stimulating parasympathetic nerves, and an initialization stimulus for preventing stimulus saturation of the sympathetic nerves or the parasympathetic nerves, and an output unit for outputting the sympathetic nerve stimulus, the parasympathetic nerve stimulus and the initialization stimulus to the subject in accordance with the stimulus pattern.

As the stimulus pattern, the pattern generating unit preferably generates a first stimulus pattern in which the initialization stimulus is outputted before and after the sympathetic nerve stimulus or the parasympathetic nerve stimulus.

Preferably, as the stimulus pattern, the pattern generating unit further generates a second stimulus pattern in which the initialization stimulus, the sympathetic nerve stimulus continuing for a first period, the parasympathetic nerve stimulus continuing for a second period, and the initialization stimulus are outputted in sequence, or a third stimulus pattern in which the initialization stimulus, the parasympathetic nerve stimulus continuing for a first period, the sympathetic nerve stimulus continuing for a second period, and the initialization stimulus are outputted in sequence, and the first period is short enough not to affect the heart rate of the subject, and the second period is longer than a period required for a heart rate response of the subject to the sympathetic nerve stimulus or the parasympathetic nerve stimulus to be saturated.

Preferably, the heart-rate control device further includes a learning unit for measuring the length of a saturation time using the heartbeat information detected in advance, the saturation time being a period required for the heart rate response of the subject to the sympathetic nerve stimulus or the parasympathetic nerve stimulus to be saturated, wherein the pattern generating unit varies the length of a period corresponding to the sympathetic nerve stimulus or the parasympathetic nerve stimulus in the first, second and third stimulus patterns as a function of the length of the saturation time.

Preferably, the learning unit further measures two or more of a base heart rate, a normal heart rate and a post-exercise heart rate of the subject in advance, and a value corresponding to a heart rate within a heart rate range of the subject is to be inputted to the input unit as the information on the target value, the heart rate range being determined by heart rates measured in advance by the learning unit.

The output unit is preferably a light emitter and emits red light, blue light and white light as the sympathetic nerve stimulus, the parasympathetic nerve stimulus and the initialization stimulus, respectively.

The output unit is preferably a heating/cooling unit to be attached to the skin of the subject, and the temperature of the heating/cooling unit is controllable between a first temperature higher than a body temperature and a second temperature lower than the body temperature and changes to the second temperature, the first temperature and the same temperature as the body temperature as the sympathetic nerve stimulus, the parasympathetic nerve stimulus and the initialization stimulus, respectively.

The output unit is preferably an audio unit and plays back a piece of music whose tempo is faster than a normal heart rate of the subject, a piece of music whose tempo is slower than the normal heart rate, and a piece of music whose tempo is as fast as the normal heart rate as the sympathetic nerve stimulus, the parasympathetic nerve stimulus and the initialization stimulus, respectively.

Preferably, a target value of the speed of the passage of subjective time is to be inputted to the input unit, the subjective time being time subjectively perceived by the subject, and the difference extracting unit extracts a difference between the target value and a current value of the speed of the passage of subjective time corresponding to a heart rate of the subject calculated from the heartbeat information.

Preferably, a target value of calorie consumption of the subject is to be inputted to the input unit, and the difference extracting unit extracts a difference between the target value and a current value corresponding to calories that will be consumed if a current heart rate of the subject calculated from the heartbeat information is maintained for a predetermined time.

Preferably, the detector is an acceleration sensor to be worn on a hand of the subject and detects periodic pulsation of the hand synchronized with a heartbeat as the heartbeat information, and a target value of intervals of the pulsation is to be inputted to the input unit, and the difference extracting unit extracts a difference between the target value and a current value of intervals of the pulsation calculated from the heartbeat information.

The output unit is preferably a sighting device and displays a line of sight or an area around the line of sight in red, blue and white as the sympathetic nerve stimulus, the parasympathetic nerve stimulus and the initialization stimulus, respectively.

The above heart-rate control device is capable of adjusting the heart rate of a subject to a desired value between a base heart rate and an active heart rate, such as a heart rate immediately after physical exercise.

BRIEF DESCRIPTION OF DRAWINGS

FIG. 9 is a diagram for explaining a heating/cooling unit 50.

FIGS. 10(A) and 10(B) show a control device 2 and a detector 10a thereof.

DESCRIPTION OF EMBODIMENTS

Hereinafter, heart-rate control devices will be described with reference to the accompanying drawings. However, note that the present invention is not limited to the drawings or the embodiments described below.

Figure 1:
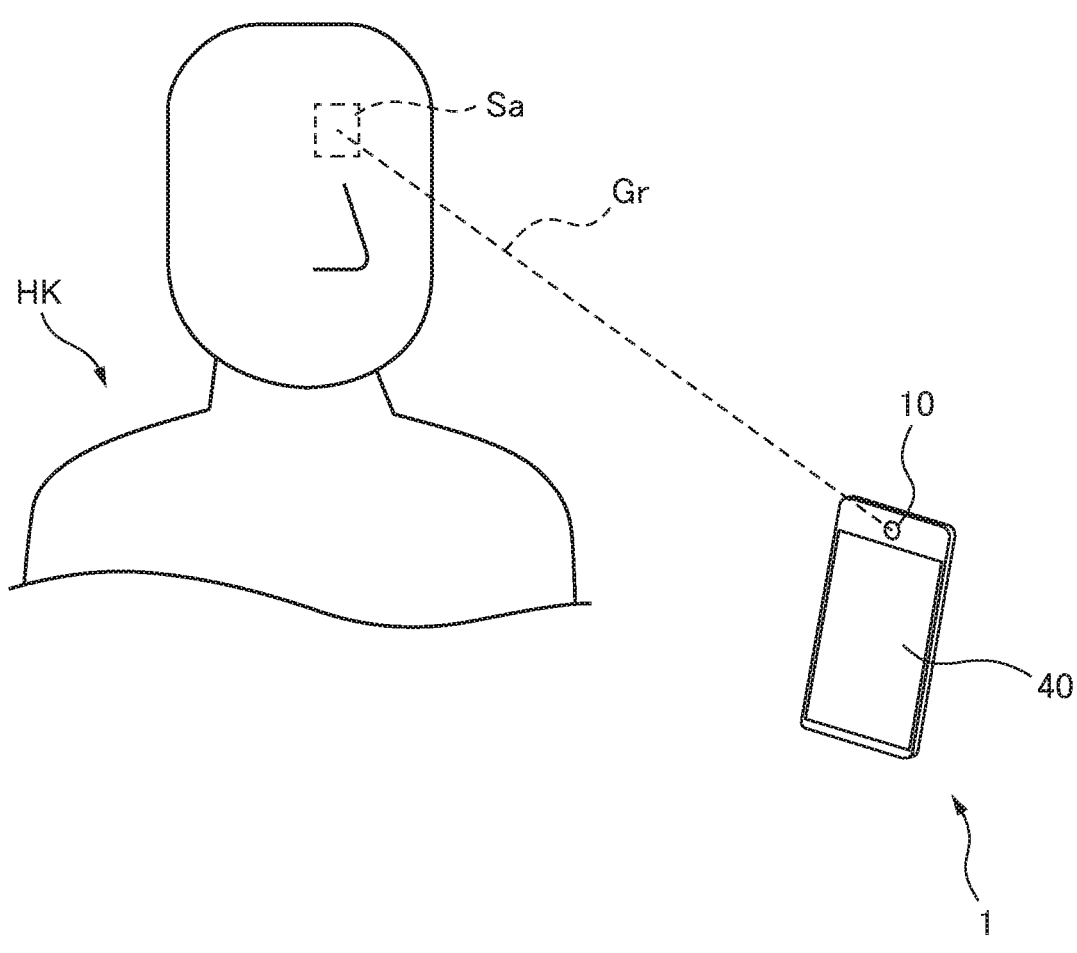
FIG. 1 is a diagram for explaining how a control device 1 is used.
Figure 2:
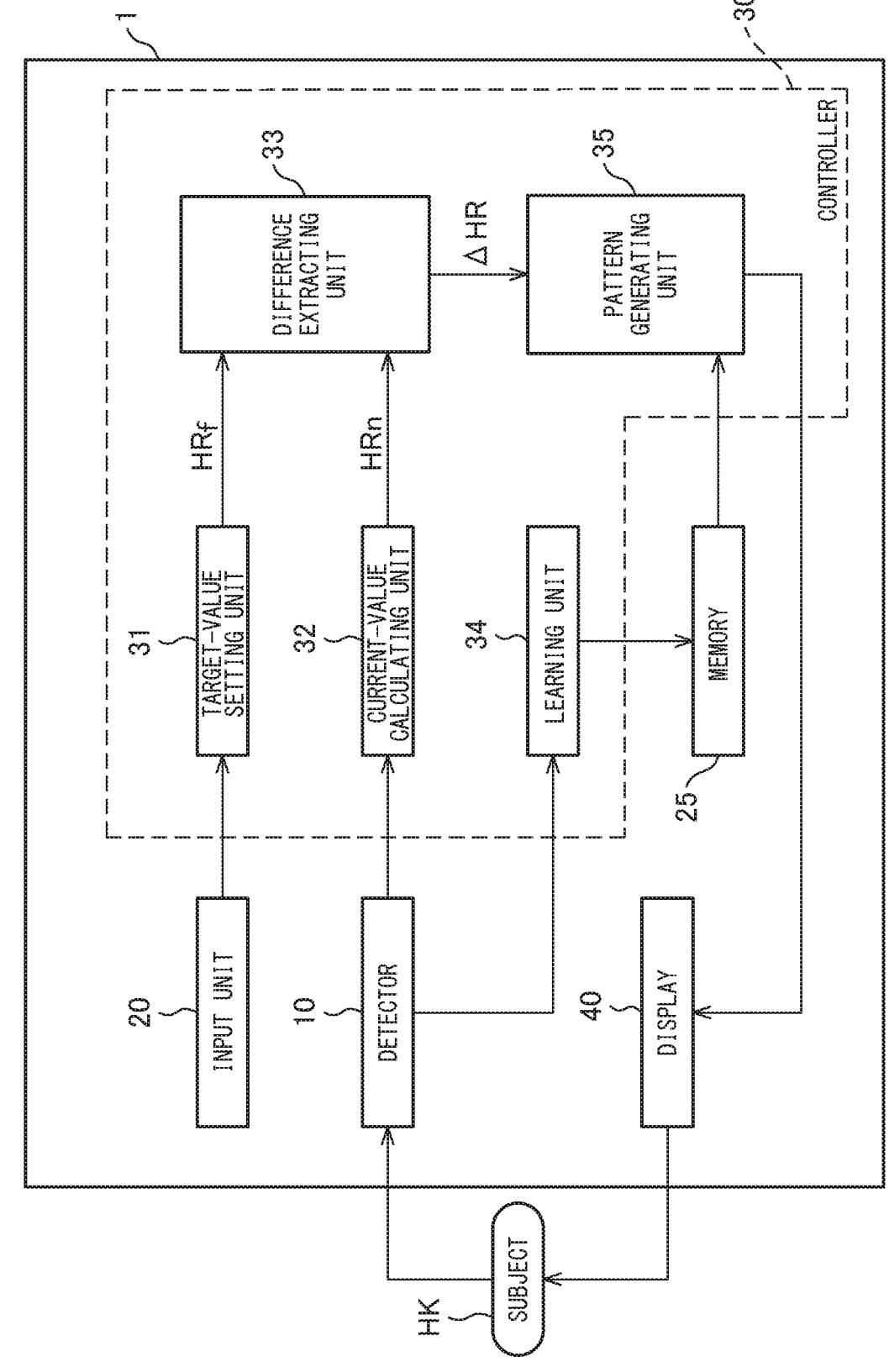
FIG. 2 is a schematic block diagram of the control device 1.

FIG. 1 is a diagram for explaining how a control device 1 is used. FIG. 2 is a schematic block diagram of the control device 1. The control device 1 includes a detector 10, an input unit 20, a memory 25, a controller 30 and a display 40. The control device 1 is an example of the heart-rate control device, detects heartbeat information of a subject HK with the detector 10, outputs to the display 40 (i.e., displays) color stimuli for stimulating sympathetic and parasympathetic nerves in order to vary the heart rate of the subject HK, and thereby controls the heart rate so as to approach a target value. Although FIG. 1 shows the case in which the control device 1 is a smartphone or a tablet device including an image capturing unit (camera), the control device 1 may be a personal computer (PC) or a specifically designed processing apparatus. The control device 1 is not limited to a portable device but may be a stationary device.

In particular, the control device 1 controls the heart rate to adjust subjective time of the subject HK. Accordingly, the relationship between heart rates and subjective time will be first described. The length of time that a human subjectively perceives varies between individuals, and some feel a certain length of time to be long while others feel it to be short. This length of time that a human subjectively perceives and varies between individuals will be referred to as "subjective time."

Figure 3:
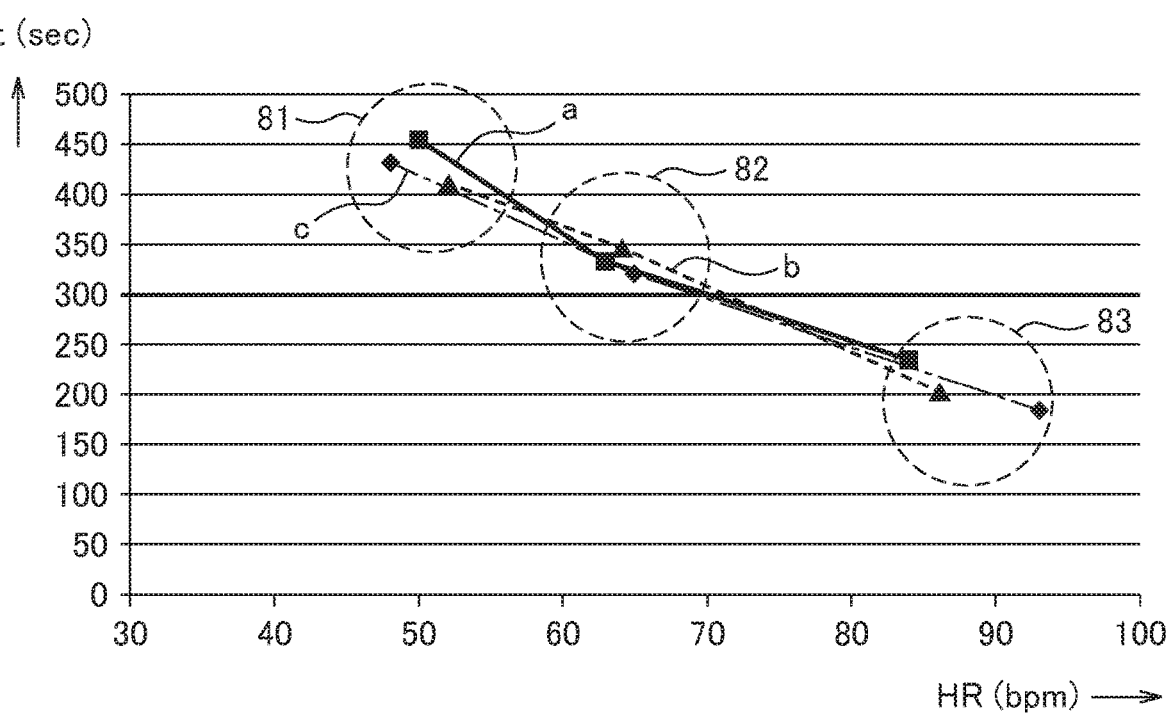
FIG. 3 is a graph showing the relationship between subjective time and heart rates.

FIG. 3 is a graph showing the relationship between subjective time and heart rates. FIG. 3 shows actually elapsed time (physical time) and heart rates measured when subjects felt that 300 seconds (5 minutes) had passed without referring to a timepiece. The abscissa represents the heart rates HR in bpm (beats per minute) of the subjects, and the ordinate represents the actually elapsed time tin seconds measured when they felt that 300 seconds (5 minutes) had passed. Curves a to c are the results for different subjects.

The area of reference numeral 81 corresponds to a state in which the heart rates are close to a base heart rate, e.g., a state immediately after getting out of bed (slow metabolism state), and at this time, the subjects perceive physical time to be approximately 1.5 times longer (i.e., feel the passage of time to be fast). The area of reference numeral 82 corresponds to a state in which the heart rates are close to one measured in a sitting position in the daytime (normal state), and at this time, the subjective time of the subjects is substantially equal to the physical time. The area of reference numeral 83 corresponds to a state in which the heart rates are high, e.g., a state immediately after physical exercise (fast metabolism state), and at this time, the subjects perceive physical time to be approximately 0.7 times shorter (i.e., feel the passage of time to be slow).

As described above, there is a correlation between subjective time and heart rates (metabolism). For example, since the heartbeat of elderly people slows down with increasing age, their subjective time flows slower than physical time, and they may feel physical time to flow fast. For this reason, it is possible to estimate current subjective time from a heart rate and to speed up or slow down the passage of subjective time by means of heart rate control. In particular, since some elderly people may quarrel with a caregiver because of a discrepancy in subjective time, it is desired that the passage of subjective time can be easily speeded up with a portable device. However, if stimuli are simply provided to sympathetic and parasympathetic nerves at random, it is difficult to adjust the heart rate to an arbitrary selected target value.

Figure 4:
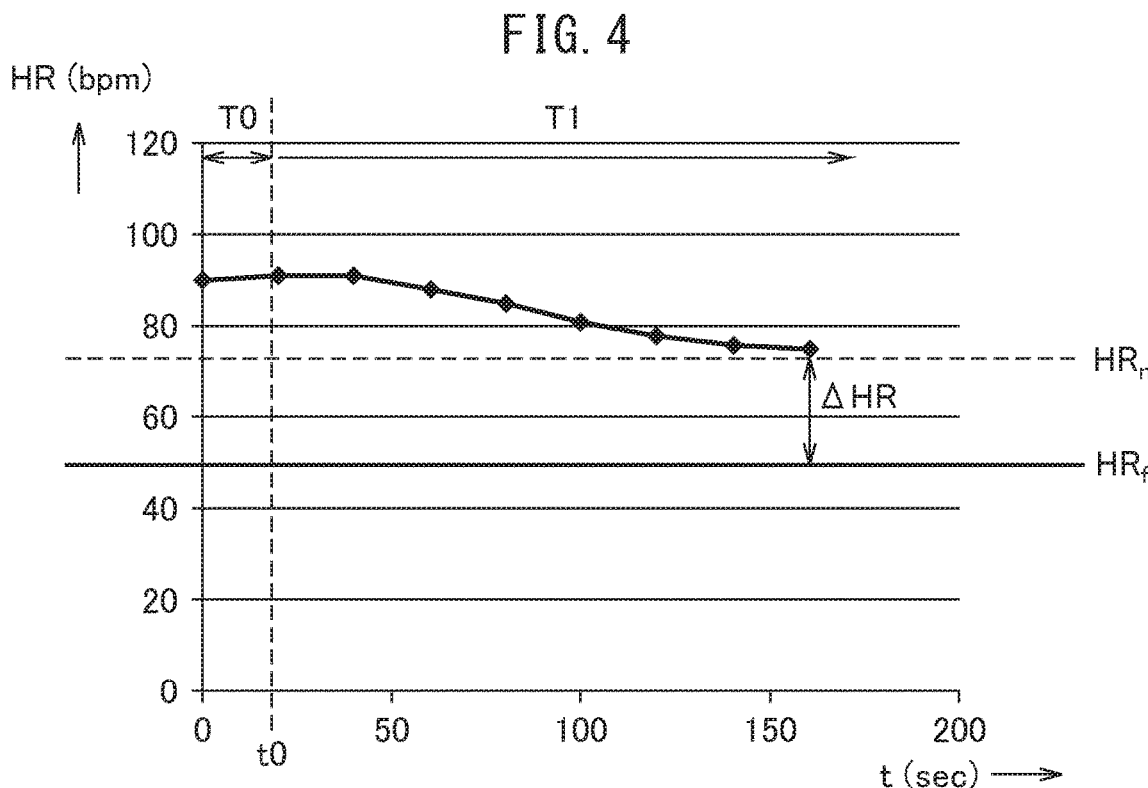
FIG. 4 is a graph for explaining how the heart rate varies over time in response to external stimuli.

FIG. 4 is a graph for explaining how the heart rate varies over time in response to external stimuli. The abscissa and ordinate represent time t in seconds and heart rate HR in bpm, respectively. The illustrated graph shows time-varying changes of the heart rate (heart rate response) for the case that a subject is illuminated with white light in the period T0 from time 0 to time t0 and with blue light, which stimulates parasympathetic nerves, in the period T1 from time t0 onward.

Even if the stimulus of blue light is maintained, parasympathetic nerves adapt thereto after a certain time, and therefore the heart rate is saturated at approximately 75 bpm ($HR_n$) after decreasing from the initial value of 90 bpm to a certain extent, and does not decrease any more. Since a decrease in the heart rate leads to stability of nerves, this change is sufficient for the purpose of stabilizing nerves. However, for example, if it is desired to adjust the heart rate to a base heart rate of 50 bpm ($HR_f$), continuing providing only the blue stimulus results in a difference $\Delta HR$ of approximately 25 bpm being left, and therefore the target value of 50 bpm cannot be reached. The same applies for the case that sympathetic nerves are stimulated with red light. Since sympathetic nerves also adapt to the stimulus after a certain time, the heart rate will be saturated after a slight increase.

In order to adjust the subjective time of a subject (user), the control device 1 provides stimuli to the subject to control his/her heart rate. To this end, the control device 1 measures the heart rate of the subject, compares the measured value (current value) with a target value to extract their difference, selects a stimulus pattern for stimulating sympathetic and parasympathetic nerves in order for the heart rate to approach the target value, and outputs stimuli to the subject in accordance with the selected stimulus pattern. In particular, in order to avoid the heart rate response being saturated due to adaption to stimuli, the control device 1 uses, as the stimulus pattern, a combination of stimuli acting on sympathetic and parasympathetic nerves separately and varying the heart rate and an initialization stimulus preventing stimulus saturation of these nerves.

FIGS. 5(A) to 5(F) are graphs for explaining examples of the stimulus pattern used by the control device 1. The abscissa and ordinate of each graph represent time t in seconds and heart rate HR in bpm, respectively. These graphs show heart rate responses for the case that a subject is illuminated with red, blue or white light. Reference symbols R, B and W indicate periods (red, blue and white periods) during which the subject is illuminated with the red, blue and white light, respectively. The red, blue and white light correspond to a sympathetic nerve stimulus for stimulating sympathetic nerves (a stimulus for activation), a parasympathetic nerve stimulus for stimulating parasympathetic nerves (a stimulus for resting), and an initialization stimulus for preventing stimulus saturation of them and for creating a nearly normal state (no stimulus), respectively.

Figure 5:
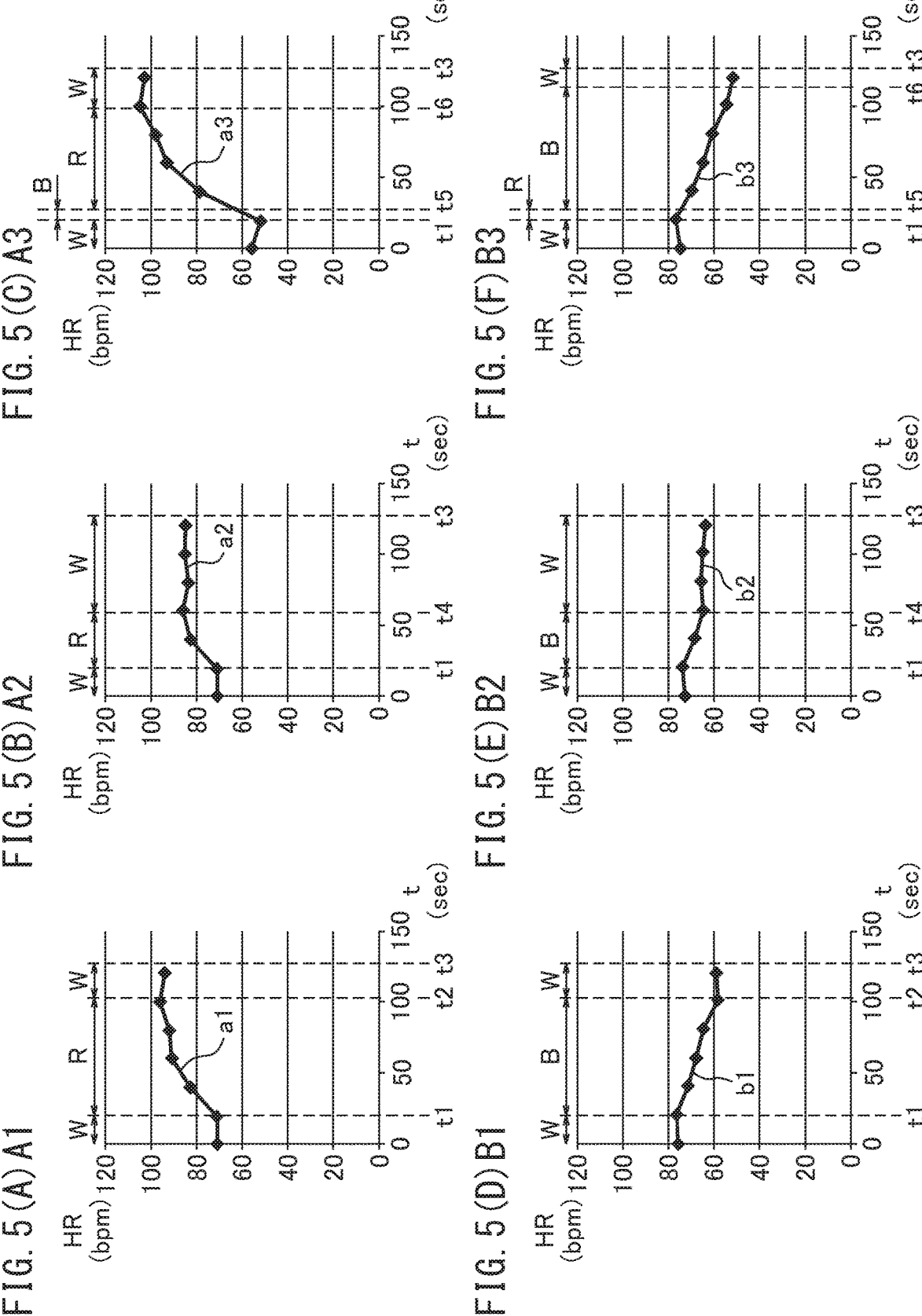
FIGS. 5(A) to 5(F) are graphs for explaining examples of the stimulus pattern used by the control device 1.

Curves a1 to a3 in FIGS. 5(A) to 5(C) show examples of the stimulus pattern for sympathetic nerves. In the pattern A1 of FIG. 5(A), an initialization stimulus of white, a sympathetic nerve stimulus of red, and an initialization stimulus of white are provided from time 0 to time t1, from time t1 to time t2, and from time t2 to time t3 (0<t1<t2<t3), respectively. In the pattern A2 of FIG. 5(B), an initialization stimulus of white, a sympathetic nerve stimulus of red, and an initialization stimulus of white are provided from time 0 to time t1, from time t1 to time t4, and from time t4 to time t3 (0<t1<t4<t3), respectively. In the pattern A3 of FIG. 5(C), an initialization stimulus of white, a parasympathetic nerve stimulus of blue, a sympathetic nerve stimulus of red, and an initialization stimulus of white are provided from time 0 to time t1, from time t1 to time t5, from time t5 to time t6, and from time t6 to time t3 (0<t1<t5<t6<t3), respectively.

The lengths of the red periods in the patterns A1 and A3 are longer than the saturation time required for the heart rate response of the subject to the corresponding stimulus to be saturated, and the length of the red period in the pattern A2 is shorter than this saturation time. The length of the blue period in the pattern A3 is short enough not to affect the heart rate, e.g., approximately 1 to 2 seconds, and is shorter than the red period in the pattern A2. The patterns A1 to A3 increase the heart rate, and the amounts of change increase in the order of the patterns A2, A1 and A3.

Curves b1 to b3 in FIGS. 5(D) to 5(F) show examples of the stimulus pattern for parasympathetic nerves. In the pattern B1 of FIG. 5(D), an initialization stimulus of white, a parasympathetic nerve stimulus of blue, and an initialization stimulus of white are provided from time 0 to time t1, from time t1 to time t2, and from time t2 to time t3, respectively. In the pattern B2 of FIG. 5(E), an initialization stimulus of white, a parasympathetic nerve stimulus of blue, and an initialization stimulus of white are provided from time 0 to time t1, from time t1 to time t4, and from time t4 to time t3, respectively. In the pattern B3 of FIG. 5(F), an initialization stimulus of white, a sympathetic nerve stimulus of red, a parasympathetic nerve stimulus of blue, and an initialization stimulus of white are provided from time 0 to time t1, from time t1 to time t5, from time t5 to time t6, and from time t6 to time t3, respectively.

The lengths of the blue periods in the patterns B1 and B3 are longer than the saturation time, and the length of the blue period in the pattern B2 is shorter than the saturation time. The length of the red period in the pattern B3 is short enough not to affect the heart rate, e.g., approximately 1 to 2 seconds, and is shorter than the blue period in the pattern B2. The patterns B1 to B3 increase the heart rate, and the amounts of change increase in the order of the patterns B2, B1 and B3.

The patterns A1, A2, B1 and B2 are examples of the first stimulus pattern. In these stimulus patterns, the initialization stimulus (W) is outputted before and after the sympathetic nerve stimulus (R) or the parasympathetic nerve stimulus (B). Since the initialization stimulus (no stimulus) initializes the saturated response to stimuli, interposing an initialization stimulus makes it possible to prevent the heart rate response from being saturated and to continue varying the heart rate even if the sympathetic nerve stimulus or the parasympathetic nerve stimulus is repeatedly provided.

The patterns A3 and B3 are an example of the third and second stimulus patterns, respectively. The length of the red period in the pattern A1 is the same as that in the pattern A3, but the amount of change in the heart rate is greater in the pattern A3 than in the pattern A1. The length of the blue period in the pattern B1 is the same as that in the pattern B3, but the amount of change in the heart rate is greater in the pattern B3 than in the pattern B1. This is because if a first stimulus that causes a change in the direction opposite to a desired (forward) direction (the parasympathetic nerve stimulus in the case of the pattern A3) is provided for only a moment, and then a second stimulus that causes a change in the forward direction (the sympathetic nerve stimulus in the case of the pattern A3) is provided for a period longer than the saturation time, the second stimulus is perceived to be greater as compared to the case in which the first stimulus is omitted. This principle is the same as the fact that if a human touches something cold and then something hot, he/she feels the latter to be hotter than it actually is.

The control device 1 generates a stimulus pattern in which some of the patterns A1 to B3 are combined as necessary in the form of sequential pulses, and outputs the corresponding stimuli in accordance with this pattern. For example, the pattern A1, A3, B1 or B3 is first used so that the current value of the heart rate may be roughly adjusted to a target value, and then the stimuli of the patterns A2 and B2 are repeatedly outputted by using pulse-width modulation (PWM). In this way, the heart rate (subjective time) can be accurately adjusted to the target value.

The components of the control device 1 shown in FIG. 2 will be described below.

The detector 10 is an image capturing unit included in the control device 1 and is constructed from, for example, a CMOS (complementary metal-oxide semiconductor) or CCD (charge-coupled device) image sensor. The detector 10 continuously captures images Gr of a measurement frame Sa in an exposed skin portion of the subject HK (e.g., a facial region, such as a forehead or cheek) automatically without being operated by the subject HK, as shown in FIG. 1. Luminance of the images Gr varies in synchronization with the blood flow of the subject HK because capillary arteries densely exist inside the skin of the subject HK in the measurement frame Sa. Accordingly, the detector 10 continuously captures the images Gr of the skin to detect heartbeat information of the subject HK. Although some elderly people are particularly frightened of measurement or unwilling to conduct a measurement including wearing a sensor for measurement, stress of the subject can be reduced by detecting the heartbeat information without touching the subject.

To the input unit 20, information on a target value relating to the heart rate of the subject is to be inputted. The input unit 20 of the control device 1 is a touch panel integrated with the display 40, but may be operation buttons that are separate from the display 40. The information on the target value may be a value of the heart rate, or a value indicating the speed of the passage of subjective time, e.g., a value indicating a 0.7-times slowdown (changing from the subjective time of the slow metabolism state to that of the normal state in FIG. 3) or a 1.5-times speedup (changing from the subjective time of the fast metabolism state to that of the normal state in FIG. 3) of the passage of subjective time. Alternatively, the information on the target value may be a value indicating what percentage of the heart rate or subjective time of the normal state of the subject or an average person the heart rate or subjective time is changed. The target value that can be inputted to the input unit 20 is a value corresponding to a heart rate within a heart rate range of the subject (between a base heart rate and an active heart rate, such as a heart rate immediately after physical exercise).

Figure 6:
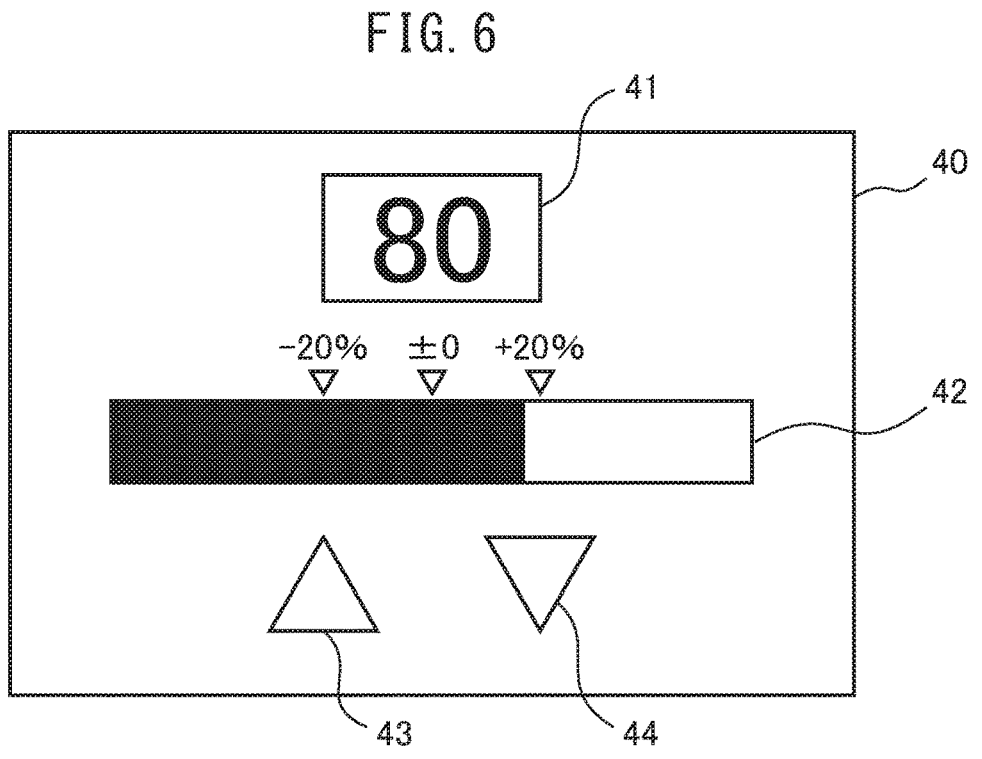
FIG. 6 shows an example of a display screen for setting a target value for heart rate control.

FIG. 6 shows an example of a display screen for setting a target value for heart rate control. In the illustrated example, the current heart rate (80 bpm) of a subject is displayed in a window 41 at the top of the screen of the display 40; an adjustment bar 42 is displayed below the window; further, an UP (increase) button 43 and a DN (decrease) button 44 are displayed below the bar. For example, the screen may be configured so that a subject (user) may touch the UP button 43 or the DN button 44 to extend or shorten the black portion of the adjustment bar 42 and thereby set the target value of the heart rate within a predetermined range, e.g., within ±20% with respect to the reference point (±0) that is, for example, the normal heart rate of the subject. Alternatively, it may be configured so that the reference point (±0) of the adjustment bar 42 is regarded as a standard value of normal heart rates corresponding to the age of the subject and that a target value may be set within a predetermined range centered at this point. It may be configured so that the length of the black portion of the adjustment bar 42 indicates the speed of the passage of subjective time and that a target value relating to the subjective time may be similarly set.

The memory 25 is, for example, a semiconductor memory and stores information necessary for the operation of the control device 1.

The controller 30 is, for example, a central processing unit (CPU) and controls the operation of the control device 1. The controller 30 includes a target-value setting unit 31, a current-value calculating unit 32, a difference extracting unit 33, a learning unit 34 and a pattern generating unit 35 as functional blocks implemented by the operation of the CPU.

The target-value setting unit 31 outputs, to the difference extracting unit 33, a target value $HR_f$ of the heart rate (or subjective time) inputted through the input unit 20. Alternatively, the target-value setting unit 31 may refer to the relationship between subjective time and heart rates shown in FIG. 3 to determine a target value of the subjective time using the inputted target value of the heart rate, and output it to the difference extracting unit 33. Alternatively, the target-value setting unit 31 may automatically set a target value of the heart rate or subjective time regardless of the presence or absence of input to the input unit 20. For example, the target-value setting unit 31 may set the target value of the subjective time so as to equal the physical time. Since the heart rate varies in times of day, the target-value setting unit 31 may automatically set the target value at different values depending on times of day so that, for example, the heart rate increases (the passage of subjective time slows down) in the morning and decreases (the passage of subjective time speeds up) in the daytime.

The current-value calculating unit 32 calculates (measures) the heart rate of the subject using the heartbeat information obtained from the detector 10 (time-series signal indicating the skin color of the subject HK). The current-value calculating unit 32 uses a band-pass filter transmitting frequencies in the range from 0.5 to 3 Hz including frequencies of human pulse waves to extract a pulse-wave signal from the component of variations in intensity of green light of the time-series signal because variations in intensity of green light of the images Gr reflect the pulse waves (variations in blood flow) most. The current-value calculating unit 32 then counts the pulse intervals of the obtained pulse wave signal to calculate the heart rate of the subject HK, and outputs this value to the difference extracting unit 33 as a current value (actually measured heart rate data) $HR_n$. Alternatively, the current-value calculating unit 32 may further refer to the relationship between subjective time and heart rates shown in FIG. 3 to estimate the subjective time corresponding to this heart rate from the calculated current value of the heart rate, and output the estimated value to the difference extracting unit 33 as the actually measured heart rate data.

The difference extracting unit 33 extracts a difference ΔHR between the current value of the heart rate of the subject obtained from the current-value calculating unit 32 and the target value of the heart rate obtained from the target-value setting unit 31, and outputs this difference to the pattern generating unit 35. Alternatively, if the difference extracting unit 33 obtains a current value and a target value relating to the subjective time from the current-value calculating unit 32 and the target-value setting unit 31, it may extract a difference between the current value and the target value relating to the speed of the passage of subjective time.

The learning unit 34 calculates the heart rate of the subject using the heartbeat information obtained from the detector 10 similarly to the current-value calculating unit 32 prior to the heart rate control being actually performed on the subject, and thereby learns the heart rate response of the subject to stimuli. Since the shapes of the graphs of the heart rate response to stimuli (curves a1 to b3 in FIGS. 5(A) to 5(F)), saturation time and saturated heart rates differ between individuals, the learning unit 34 determines, for example, the curves a1 to b3 of the heart rate response, saturation time and saturated heart rates for each subject. The learning unit 34 stores information on the heart rate response of each subject obtained by learning in the memory 25 in association with the corresponding subject.

The learning unit 34 further calculates heart rates of the subject including a base heart rate (heart rate immediately after getting out of bed), a normal heart rate, and an active heart rate, such as a heart rate immediately after physical exercise, prior to the heart rate control being actually performed on the subject, and thereby determines the range of the heart rate that can be inputted as a target value. In other words, the target value of the heart rate is a value within the heart rate range of the subject determined by the heart rates measured in advance by the learning unit 34. The heart rates to be learned may be one or two of the above-mentioned three values, but calculating all of the three values allows for accurately grasping the heart rate range of the subject. Alternatively, for example, if the normal heart rate is separately measured at regular intervals, a predetermined range centered at the normal heart rate may be regarded as the heart rate range of the subject, instead of the learning unit 34 learning the base heart rate, the normal heart rate and the active heart rate.

The pattern generating unit 35 generates a stimulus pattern depending on the difference extracted by the difference extracting unit 33 so that the current value of the heart rate may approach the target value, the stimulus pattern being a combination of a sympathetic nerve stimulus, a parasympathetic nerve stimulus and an initialization stimulus; the pattern generating unit 35 outputs this stimulus pattern to the display 40. This stimulus pattern is a combination of the patterns A1 to B3 in FIGS. 5(A) to 5(F) determined by the heart rate response learned by the learning unit 34 in advance. The lengths of the red and blue periods in the patterns A1 to B3 are adjusted in accordance with the length of the saturation time and the saturated heart rates learned by the learning unit 34. The pattern generating unit 35 determines the combination of the patterns A1 to B3 and the length of the whole stimulus pattern in accordance with the difference of the heart rate (subjective time), and controls the current subjective time so as to equal the target subjective time.

The display 40 is, for example, a liquid crystal display. The display 40 is an example of the output unit (light emitter) and emits red light, blue light and white light as the sympathetic nerve stimulus, the parasympathetic nerve stimulus and the initialization stimulus, respectively, in accordance with the stimulus pattern generated by the pattern generating unit 35. For example, the display 40 changes the color of the wallpaper in the display screen to red, blue and white to output the respective stimuli to the subject.

Alternatively, an LED (light-emitting diode) lighting apparatus may be used as the output unit separately from the display 40. In this case, for example, red, green and blue LEDs respectively having peak wavelengths of approximately 630 nm, 530 nm and 460 nm may be used, and the red, blue and white light may be emitted by the red and blue LEDs and by mixing the colors of these three LEDs. The LED lighting apparatus of this case is not limited to one included in the control device 1 but may be, for example, one placed in a room.

Figure 7:
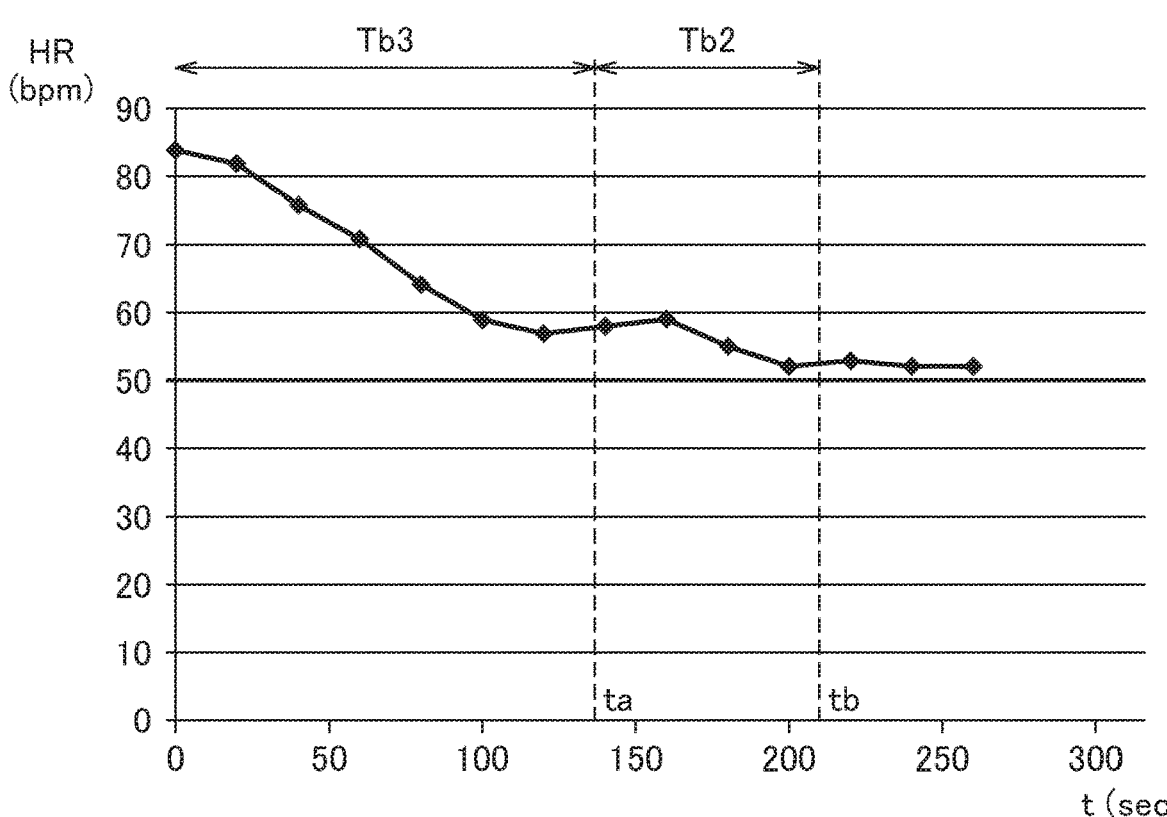
FIG. 7 is a graph showing an example of the heart rate control performed by the control device 1.

FIG. 7 is a graph showing an example of the heart rate control performed by the control device 1. The abscissa and ordinate represent time t in seconds and heart rate HR in bpm, respectively. FIG. 7 shows an example in which the target value of the heart rate is approximately 50 bpm, and the heart rate, which is approximately 84 bpm at time 0, is adjusted to approximately 50 bpm. In this example, the heart rate is greatly reduced by the parasympathetic nerve stimulus of the pattern B3 in the period Tb3 from time 0 to time ta, and further slightly reduced by the parasympathetic nerve stimulus of the pattern B2 in the period Tb2 from time ta to time tb (0<ta<tb). Thus, the speed of the passage of subjective time, which is approximately 0.7 times that of physical time at time 0, becomes approximately 1.5 times that of physical time after the adjustment. In this way, the subjective time (heart rate) can be arbitrarily controlled by color stimuli in which the patterns A1 to B3 are appropriately combined.

Figure 8:
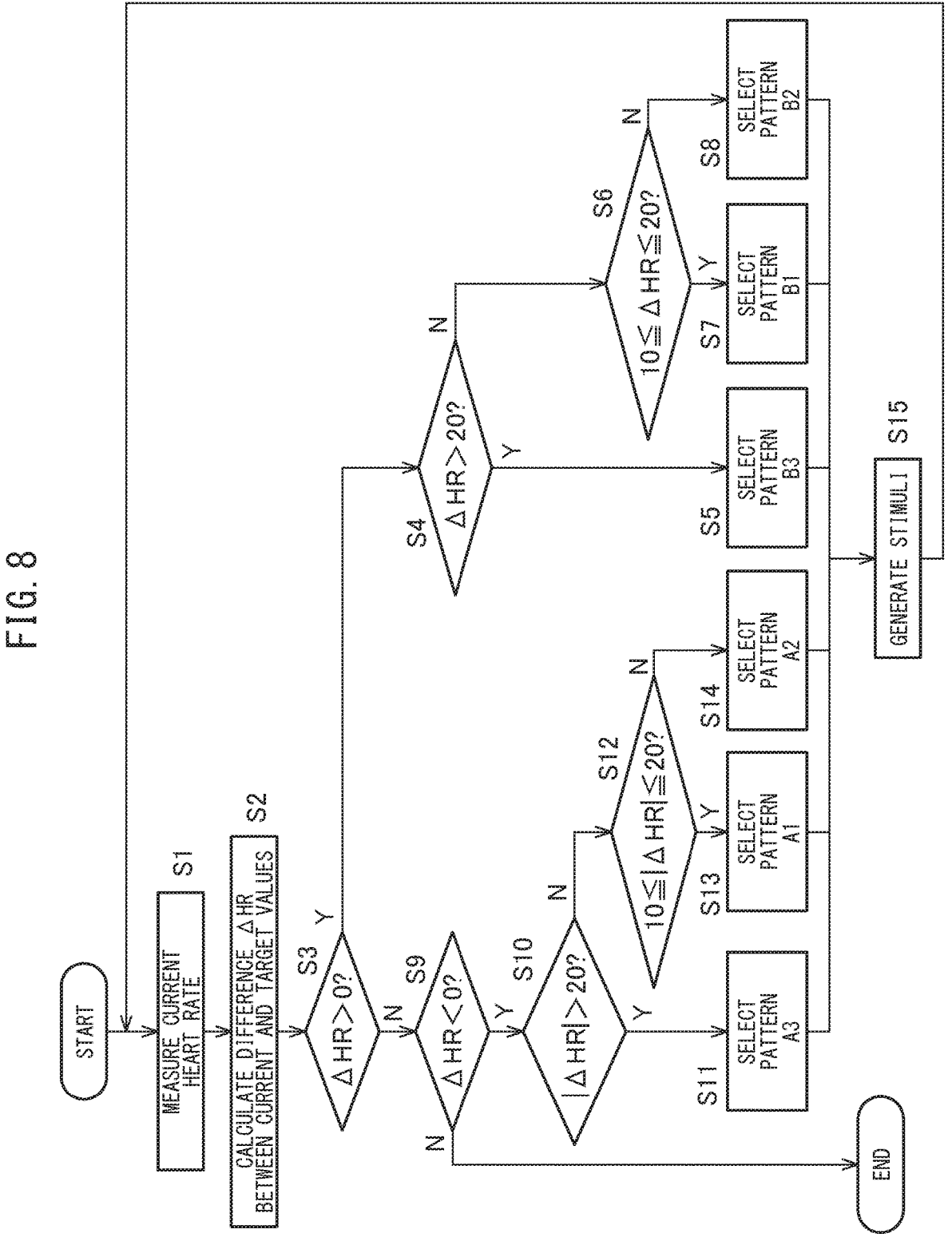
FIG. 8 is a flowchart showing an operational example of the control device 1.

FIG. 8 is a flowchart showing an operational example of the control device 1. The illustrated flow is executed by the CPU in the controller 30.

First, using the heartbeat information obtained from the detector 10, the current-value calculating unit 32 measures the current heart rate of the subject (S1). In the control device 1, a target heart rate is inputted in advance, and a target value corresponding thereto is set by the target-value setting unit 31. The difference extracting unit 33 calculates a difference ΔHR between the current heart rate obtained in S1 and the target value (=current value−target value) (S2).

If the difference ΔHR is positive (Yes in S3), the stimulus patterns for parasympathetic nerves are selected, and the process proceeds to S4. If the difference ΔHR is more than 20 bpm (Yes in S4), the pattern generating unit 35 selects the pattern B3 (S5). If the difference ΔHR is not less than 10 bpm and not more than 20 bpm (No in S4 and Yes in S6), the pattern generating unit 35 selects the pattern B1 (S7). If the difference ΔHR is less than 10 bpm (No in S6), the pattern generating unit 35 selects the pattern B2 (S8).

If the difference is negative (No in S3 and Yes in S9), the stimulus patterns for sympathetic nerves are selected, and the process proceeds to S10. If the absolute value of the difference ΔHR is more than 20 bpm (Yes in S10), the pattern generating unit 35 selects the pattern A3 (S11). If the absolute value of the difference ΔHR is not less than 10 bpm and not more than 20 bpm (No in S10 and Yes in S12), the pattern generating unit 35 selects the pattern A1 (S13). If the absolute value of the difference ΔHR is less than 10 bpm (No in S12), the pattern generating unit 35 selects the pattern A2 (S14).

If the pattern A2 or B2 is selected in S14 or S8, the pattern generating unit 35 may repeat the same pattern by using pulse-width modulation (PWM). After S5, S7, S8, S11, S13 or S14, the pattern generating unit 35 outputs the selected stimulus pattern to the display 40, and the display 40 generates color stimuli in accordance with this stimulus pattern (S15). Thereafter, the process returns to S1, and the above-described steps are repeated. Then, if the difference ΔHR becomes 0 (No in S9), the control device 1 terminates the operation.

The thresholds of the difference ΔHR used when the pattern generating unit 35 selects one of the patterns A1 to B3 are not limited to 10 bpm and 20 bpm in the above description, but may be appropriately set. Even if the difference ΔHR does not become exactly zero, the operation may be terminated when the difference becomes substantially zero, e.g., several bpm.

Since there is a correlation between heart rates and metabolism of a human as described above, control of the heart rate with the control device 1 leads to an increase in resting metabolism. In other words, an increase in the heart rate allows metabolism to speed up, thereby increasing calorie consumption without doing physical exercise. For this reason, the control device 1 can be used not only for controlling the subjective time of elderly people, but also for normalizing or improving metabolism in order to assist a person who tries to lower his/her weight or has a menopausal disorder. Accordingly, the relationship between heart rates and calorie consumption will be described below.

The calorie consumption is obtained from heart rates through an exercise intensity (% HRR) and METs (METabolic equivalents) as follows.

(1) The exercise intensity is calculated from an exercise heart rate $HR_x$, a resting heart rate $HR_0$ and a maximum heart rate $HR_{max}$ (bpm) as in the following expressions (Karvonen Formula).

$$\text{Exercise intensity (\% HRR)} = ((HR_x - HR_0)/(HR_{max} - HR_0)) \times 100$$

$$HR_{max} = 220 - \text{age}$$

(2) METs is a value indicating the intensity of physical exercise and is calculated from the exercise intensity as in the following expression.

$$\text{METs} = ((\% \text{ HRR}/10) \times \alpha) - \beta$$

The factor α is 1.2, 1.0, 0.8 and 0.5 for ages 20 to 39, 40 to 64, 65 to 79, and 80 or older, respectively. The factor β is 0 for men and 1 for women.

(3) The calorie consumption is calculated from the METs, an exercise time (h) and a weight (kg) as in the following expression.

$$\text{Calorie consumption (kcal)} = 1.05 \times \text{METs} \times (\text{exercise time}) \times \text{weight}$$

For example, if a man whose resting heart rate, age and weight are 65 bpm, 54 and 62 kg did physical exercise for an hour and kept the exercise heart rate at 80 bpm, the calorie consumption is calculated as in the following expressions.

$$\text{Exercise intensity (\% HRR)} = ((80-65)/((220-54)-65)) \times 100 = 14.85 \tag{1}$$

$$\text{METs} = ((14.85/10) \times 1.0) - 0 = 1.485 \tag{2}$$

$$\text{Calorie consumption (kcal)} = 1.05 \times 1.485 \times 1 \times 62 = 96.7 \tag{3}$$

For example, a rice ball sold in stores is approximately 150 kcal, and therefore, according to calculations, if a heart rate of 80 bpm can be maintained for two hours, calories corresponding to a little more than a rice ball can be consumed.

In view of the above, the target value inputted to the input unit 20 is not limited to a heart rate or subjective time, but may be an exercise intensity, METs or calorie consumption of pseudo-exercise realized by controlling (increasing) the heart rate. In this case, the current-value calculating unit 32 or the difference extracting unit 33 calculates the exercise intensity, METs or calorie consumption from the heart rate, and the difference extracting unit 33 may extract a difference between the current value and the target value regarding the exercise intensity, METs or calorie consumption. The calorie consumption of this case corresponds to calories that will be consumed if the current heart rate calculated from the heartbeat information is maintained for a predetermined time.

The sympathetic nerve stimulus and the parasympathetic nerve stimulus are not limited to color stimuli but may be thermal or auditory stimuli. Accordingly, a description will be given below of examples of the output unit that outputs thermal or auditory stimuli.

FIG. 9 is a diagram for explaining a heating/cooling unit 50. In the illustrated example, the heating/cooling unit 50 is attached to a neckband 51 and affixed to the skin of the back of the neck where cells sensing warmth densely exist. The heating/cooling unit 50 includes a Peltier device and a heater therein, and its temperature is controllable, for example, between 40° C. (first temperature), which is higher than the body temperature (36° C.), and 20° C. (second temperature), which is lower than the body temperature. The heating/cooling unit 50 is an example of the output unit and is controlled so that its own temperature may change, thereby providing thermal stimuli to those cells of the subject which sense warmth.

In the case of the heating/cooling unit 50, for example, the sympathetic nerve stimulus is a stimulus of 20° C. (cool); the parasympathetic nerve stimulus is a stimulus of 40° C. (warm); the initialization stimulus is a stimulus of 36° C. (no stimulus). Accordingly, the temperature of the heating/cooling unit 50 changes to 20° C., 40° C. and 36° C. during the red, blue and white periods, respectively, in the patterns A1 to B3 shown in FIGS. 5(A) to 5(F). Since the heating/cooling unit 50 is affixed only to a limited area of the skin of the subject without controlling the room temperature, thermal stimuli can be provided without annoying the subject.

FIGS. 10(A) and 10(B) show a control device 2 and a detector 10a thereof. As shown in FIG. 10(A), the control device 2 includes a small disk-shaped body 2a and an arc-shaped ear hook 2b extending from the side surface of the body. The body 2a includes a small-sized speaker 60, and the ear hook 2b includes a detector 10a. The control device 2 is an example of the heart-rate control device and is to be worn on an ear of a subject like an earphone to provide auditory stimuli, thereby controlling the heart rate of the subject. The control device 2 has the same structure and functions as the above control device 1, except that they have different outward appearances and that the detector 10, the input unit 20 and the display 40 are replaced with the detector 10a, operation buttons (not shown) and the speaker 60, respectively.

The detector 10a includes a pair of sensor pieces 11 and 12, and the control device 2 is to be worn on an ear of the subject with an earlobe of the subject pinched between the sensor pieces 11 and 12. Inside the sensor pieces 11 and 12, the detector 10a includes an optical pulse-wave sensor composed of a light emitter 17, a light receiver 18 and a light shield 19 that are shown in FIG. 10(B). For example, the light emitter 17 is an infrared LED and emits infrared light toward an earlobe 91. The light receiver 18 is a photodiode, receives light reflected from the earlobe 91, and converts variations in the amount of reflected light caused by pulsation of the blood flow in capillary vessels 92 inside the earlobe 91 to an electric signal. The light shield 19 is disposed between the light emitter 17 and the light receiver 18 so that light from the light emitter 17 may not directly enter the light receiver 18. The detector 10a detects pulse waves of the subject on the basis of variations in intensity of the received light. Since the pulse waves result from the blood flow synchronized with electrocardiograms, detection of the pulse waves allows for measuring a heart rate.

The speaker 60 is an example of the output unit and the audio unit, includes a circuit for voice synthesis (not shown), and provides auditory stimuli to the subject. In the case of the control device 2, for example, the sympathetic nerve stimulus is a piece of music whose tempo is faster than a normal heart rate of the subject; the parasympathetic nerve stimulus is a piece of music whose tempo is slower than the normal heart rate; the initialization stimulus is a piece of music whose tempo is approximately as fast as the normal heart rate. Accordingly, the speaker 60 plays back pieces of music whose tempos are approximately as fast as an active heart rate, a base heart rate and a normal heart rate during the red, blue and white periods, respectively, in the patterns A1 to B3 shown in FIGS. 5(A) to 5(F).

The detector of the control device 1 may also be an optical pulse-wave sensor, such as shown in FIG. 10(B), and on the contrary, the detector 10 of the control device 2 may also be one detecting heartbeat information by means of image capturing. Alternatively, the detectors of the control devices 1 and 2 may be, for example, a microwave Doppler sensor that can sense a heartbeat without touching the subject, or a sensor including electrodes to be worn all the time. The detector may be separate from the control device. For example, in the case of the optical pulse-wave sensor, the detector may be a mouse-shaped or watch-shaped one that detects pulse waves of a wrist or a fingertip, or in the case of detecting heartbeat information by means of image capturing, the detector may be a digital camera. For example, if the detector is a mouse-shaped pulse-wave sensor and the control device is a PC, a subject who is using the PC can be provided with color stimuli (change of the colors of the wallpaper in the display screen), thermal stimuli or auditory stimuli to control his/her heart rate.

Figure 11:
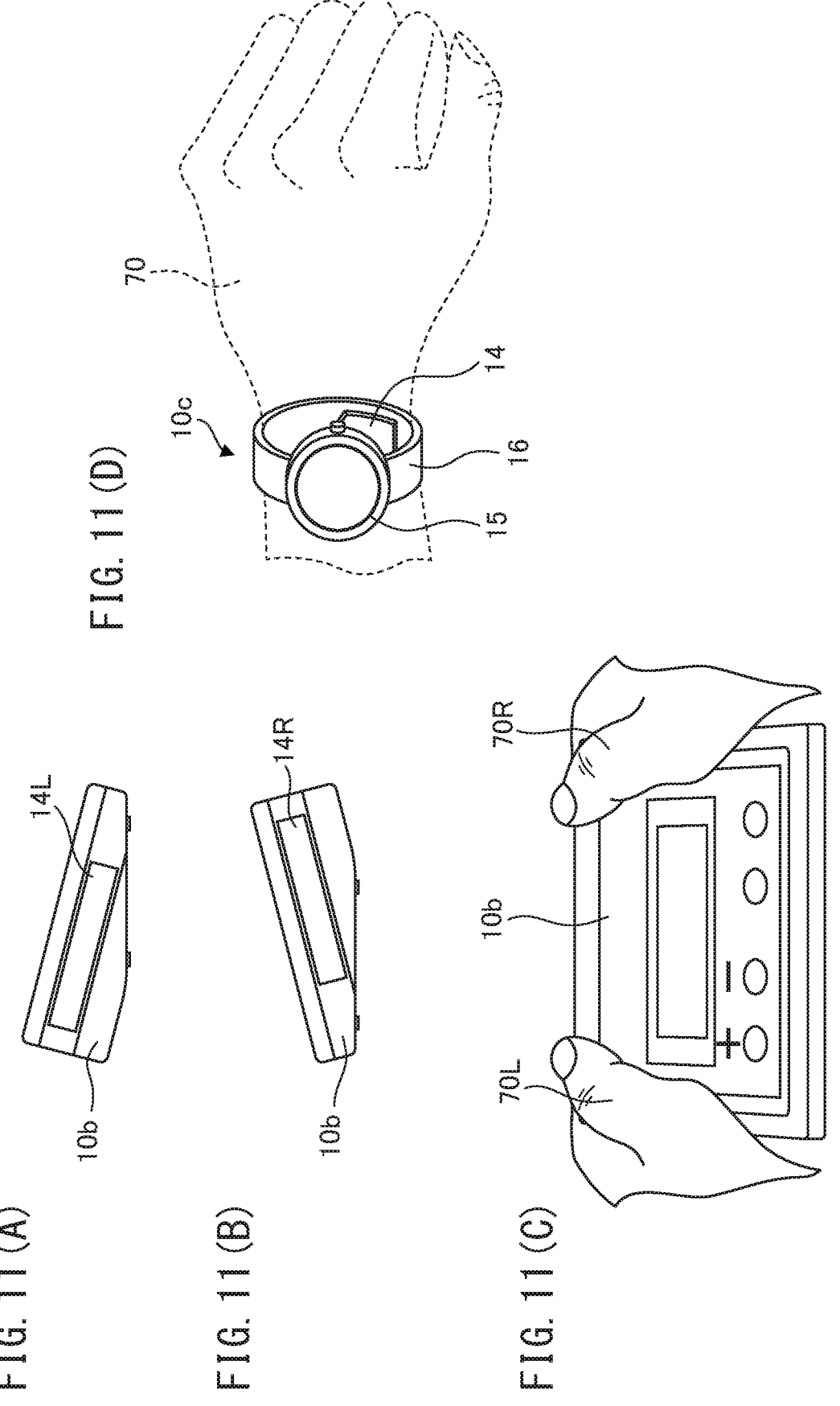
FIGS. 11(A) to 11(D) show detectors 10b and 10c.

FIGS. 11(A) to 11(D) show detectors 10b and 10c. The detector 10b shown in FIGS. 11(A) to 11(C) includes a pair of electrodes 14L and 14R for sensing electrocardiograms. As shown in FIGS. 11(A) and 11(B), the electrodes 14L and 14R are provided on the left and right side surfaces of the housing of the detector 10b, respectively. The detector 10b senses an electrocardiogram of a subject while the subject holds the housing thereof with both hands so that the left hand 70L and the right hand 70R may touch the electrodes 14L and 14R, respectively, as shown in FIG. 11(C). As described above, the detector for detecting heartbeat information is not limited to one detecting pulse waves by means of image capturing but may be a sensor including electrodes. Further, the electrode-type sensor, such as the detector 10b, may be provided with a band, for example, on the upper surfaces of the electrodes so that the subject can easily hold it for a long time.

The detector 10c shown in FIG. 11(D) is a watch-shaped pulse-wave sensor. The detector 10c includes a pulse-wave sensor 14 on the back surface of the watch. While a user wears a band 16 of the watch on a hand 70, the detector 10c senses pulse waves and shows a measured value on a time display 15 of the watch. The watch-shaped sensor, such as the detector 10c, allows the subject to wear it without an uncomfortable feeling and to detect heartbeat information.

If a human raises an arm and stops moving, body tremors (pulsation) synchronized with the heartbeat occur. The intervals of the body tremors are approximately 1 second each when the heart rate is 60 bpm, but they become several hundred milliseconds when the heart rate is higher. For example, precise soldering, tweezers work, target shooting and archery require a precise motion on the order of millimeters, and such a small motion takes a time on the order of several hundred milliseconds. For this reason, when the heart rate is more than 60 bpm, the arms move due to body tremors, which may easily result in an error in the motion.

Figure 12:
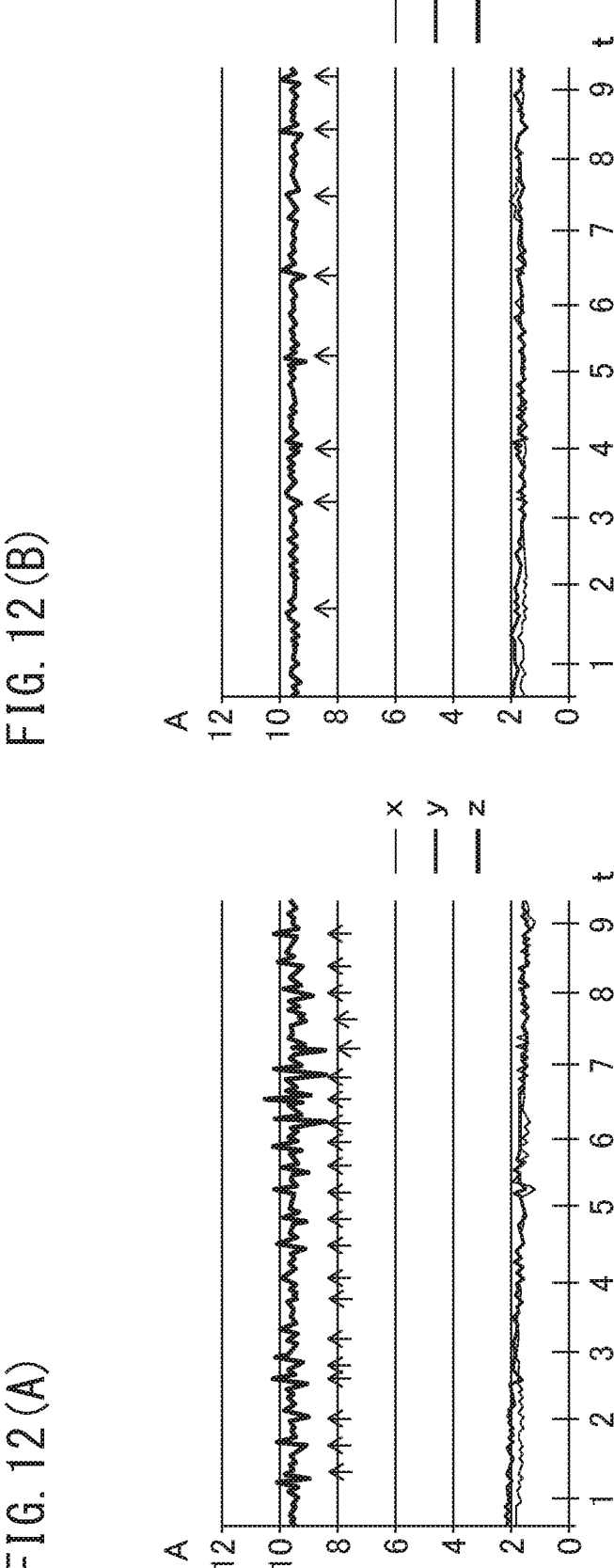
FIGS. 12(A) and 12(B) are graphs showing examples of variations in acceleration of a raised wrist.

FIGS. 12(A) and 12(B) are graphs showing examples of variations in acceleration of a raised wrist. These graphs show time-varying changes of signals outputted from an acceleration sensor worn on a wrist of a subject who kept the arm raised. The abscissa t is time in seconds, and the ordinate A is the output of the acceleration sensor in millivolts. Curve z corresponds to the component of the vertical direction (z direction), and curves x and y correspond to the components of two directions (x and y directions) perpendicular to each other in the horizontal plane. FIGS. 12(A) and 12(B) show the results of measurement for the cases that the heart rates of the subject are 150 bpm and 53 bpm, respectively.

Variations in amplitude indicated by arrows in the graphs correspond to body tremors, and these results show that the body tremors can be detected with an acceleration sensor. Since the variations in amplitude are greater in the z direction than in the x and y directions, it can be seen that the body tremors occur mainly in the vertical direction when an arm is kept raised. The intervals between the arrows are wider in FIG. 12(B) than in FIG. 12(A), and the intervals of the body tremors are on the order of several hundred milliseconds in FIG. 12(A), in which the heart rate is 150 bpm, but are approximately 1 second in FIG. 12(B), in which the heart rate is 53 bpm. This shows that a lower heart rate results in wider intervals of body tremors.

In order to improve the accuracy of precise work using hands, it is necessary to lower the heart rate to widen the intervals of body tremors, and then act between the body tremors. For example, some shooters of target shooting do high-altitude training or take medicine to lower the heart rate in order to reduce body tremors. However, for a person doing precision work, it is desired that body tremors resulting from the heartbeat can be reduced in an easier way. Accordingly, a description will be given below of an example in which the above heart-rate control device is used for precision work for the purpose of reducing body tremors resulting from the heartbeat.

Figure 13:
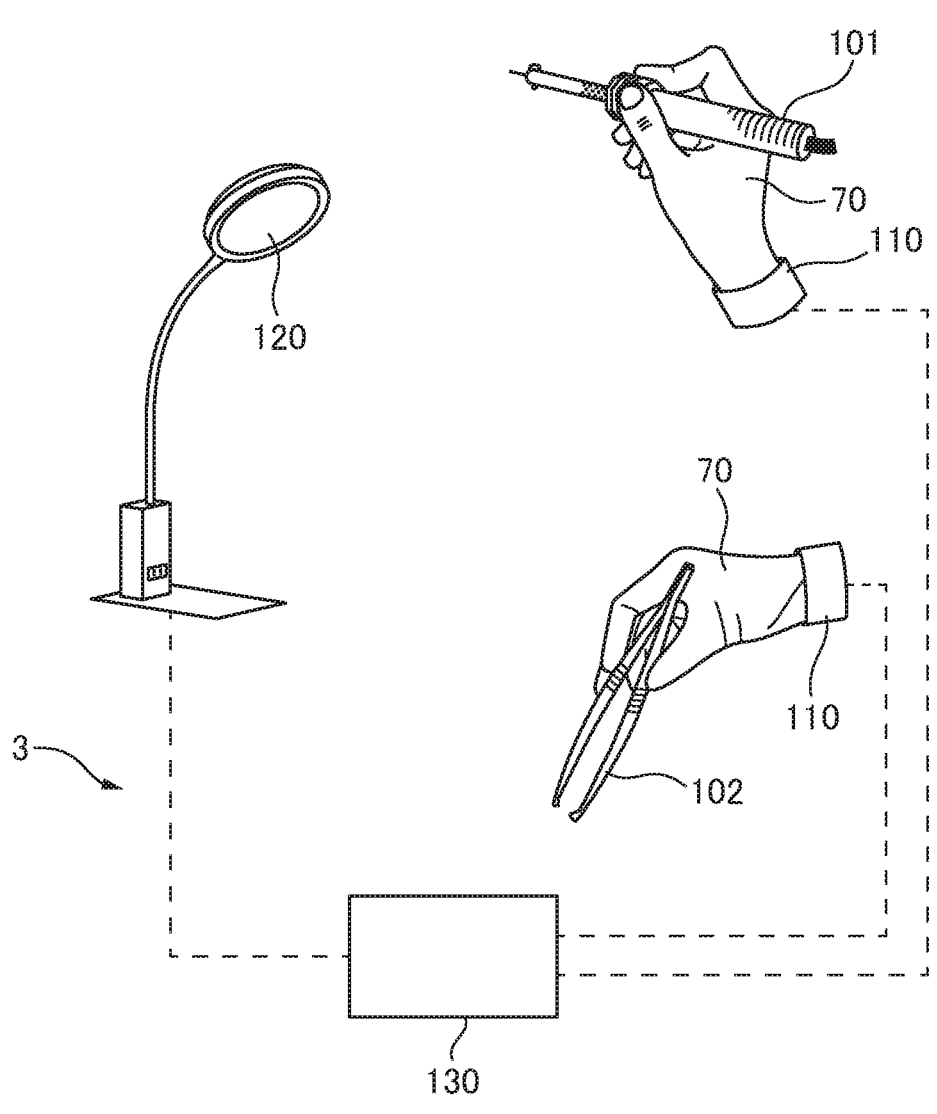
FIG. 13 is a diagram schematically illustrating the configuration of a control device 3 and an example of its usage.

FIG. 13 is a diagram schematically illustrating the configuration of a control device 3 and an example of its usage. The control device 3 is composed of a detector 110, a light emitter 120 and a control terminal 130. The control device 3 is an example of the heart-rate control device, detects pulsation of a hand of an operator (subject) who is using, for example, a soldering iron 101 or tweezers 102, and outputs color stimuli to the operator to adjust (decrease) his/her heart rate to a target value, thereby reducing body tremors of the operator.

The detector 110 is, for example, a wristband-shaped acceleration sensor and is worn on a hand 70 (wrist) of an operator who is holding the soldering iron 101 or the tweezers 102. As the heartbeat information, the detector 110 detects periodic pulsation of the hand 70 synchronized with the heartbeat and outputs the detection signal to the control terminal 130. As in this case, the heartbeat information detected by the detector is not limited to heart rates or pulse rates (electrocardiograms or pulse waves) but may be body tremors of the subject. The body part on which the detector is worn is not limited to a wrist but may be the back of a hand, a finger, an arm or the like.

The light emitter 120 is a lighting apparatus including, for example, LEDs that can emit red, blue and white light, and in the illustrated example, it is an electric lamp on a desk used by an operator for his/her work. The light emitter 120 is an example of the output unit and emits red light, blue light and white light as the sympathetic nerve stimulus, the parasympathetic nerve stimulus and the initialization stimulus, respectively, in accordance with the stimulus pattern generated by the control terminal 130. The light emitter 120 may be one specifically designed for the control device 3, or an electric lamp in a room or an electric light mounted on a ceiling may be used as the light emitter 120. Alternatively, the stimuli provided to the operator are not limited to color stimuli generated by the light emitter 120 but may be thermal or auditory stimuli generated by the heating/cooling unit 50 in FIG. 9 or the speaker 60 in FIG. 10(A).

The control terminal 130 includes the same functional blocks as the controller 30 of the control device 1 shown in FIG. 2 and communicates with the detector 110 and the light emitter 120 through a wired or wireless network to control the operation of the control device 3. The control terminal 130 may be, for example, a portable device to be worn by an operator or a stationary device placed in a workspace. Unlike the illustrated example, the control terminal 130 may be integrated with the detector 110 or the light emitter 120.

The control terminal 130 also serves as an input unit of the control device 3 and includes operation buttons for an operator to input information on a target value relating to a heart rate. In the control device 3, for example, a target value of the intervals of body tremors (pulsation) is inputted to the control terminal 130 by an operator (subject). Alternatively, this target value may be set in advance at the length of time corresponding to the base heart rate of the operator regardless of the presence or absence of input to the input unit. Instead of the target value, the age of the operator or other parameters may be inputted to the control terminal 130, and the control terminal 130 may set the target value at the length of time matching the heart rate corresponding to the inputted age. The target value in the control device 3 is preferably approximately 60 bpm so that each interval of body tremors will be 1 second or longer.

The target-value setting unit 31 of the control device 3 outputs the target value of the intervals of pulsation to the difference extracting unit 33. The current-value calculating unit 32 obtains the detection signal from the detector 110, detects peaks (points indicated by arrows in FIGS. 12(A) and 12(B)) in the detected waveform of the z direction, and measures the intervals between these peaks. The current-value calculating unit 32 measures the intervals of pulsation in this way multiple times and outputs the average of the obtained values to the difference extracting unit 33 as the current value of the intervals of pulsation. The difference extracting unit 33 extracts a difference between the current value obtained from the current-value calculating unit 32 and the target value obtained from the target-value setting unit 31 regarding the intervals of pulsation and outputs this difference to the pattern generating unit 35. The pattern generating unit 35 generates a stimulus pattern depending on the difference extracted by the difference extracting unit 33 so that the current value of the intervals of pulsation may approach the target value, the stimulus pattern being a combination of a sympathetic nerve stimulus, a parasympathetic nerve stimulus and an initialization stimulus; the pattern generating unit 35 outputs this stimulus pattern to the light emitter 120.

The operation flow of the control device 3 is the same as that of the control device 1, except that S1 in the flow of FIG. 8 is replaced with "measure current pulsation intervals of wrist." The time required for a human to make a small motion is generally on the order of several hundred milliseconds, and therefore if the heart rate is lowered to extend the intervals of body tremors to approximately 1 seconds (60 bpm) or longer with the control device 3, the operator can make a necessary motion therebetween without being affected by the body tremors.

Figure 14:
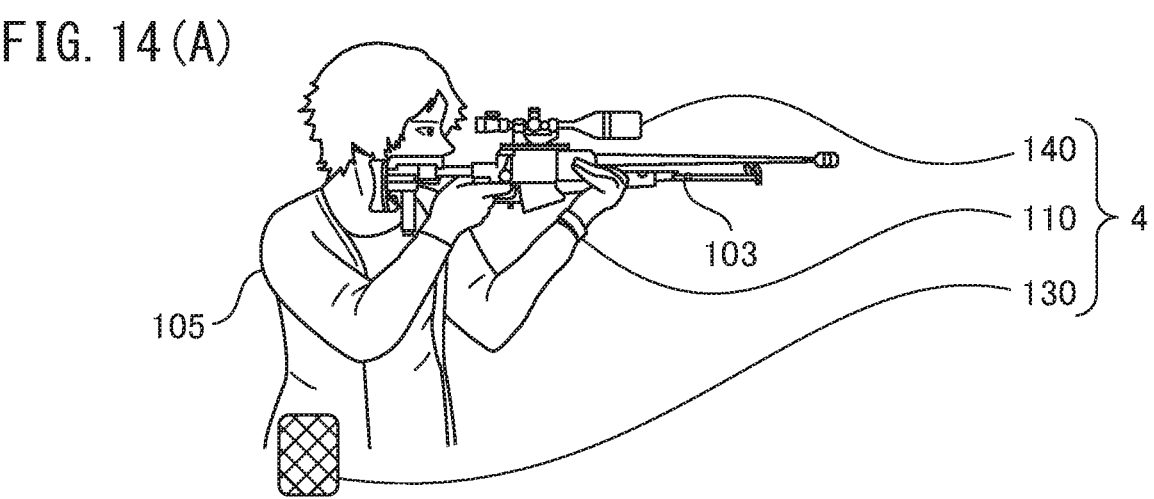
FIGS. 14(A) to 14(C) are diagrams schematically illustrating the configuration of a control device 4 and an example of its usage.
Figure 14:
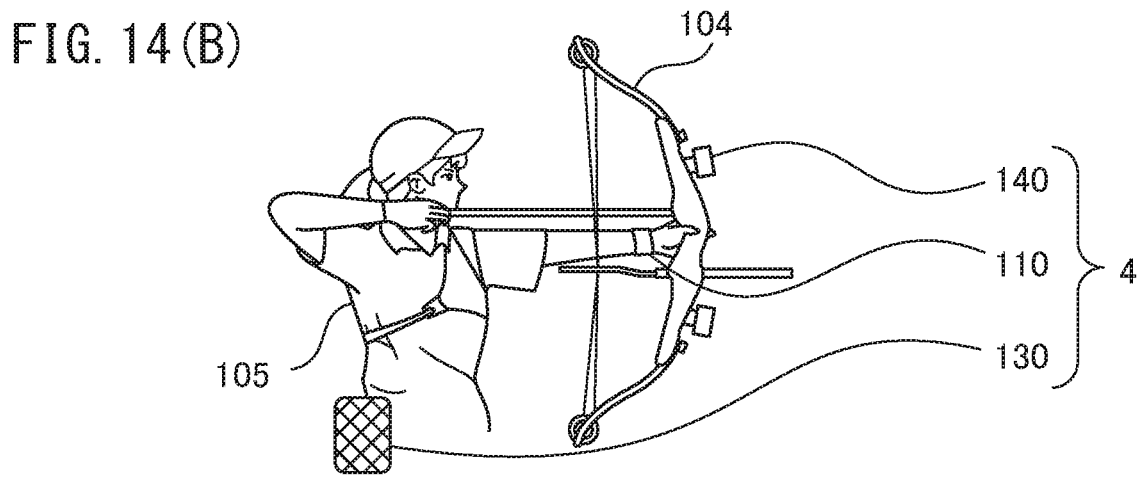
Figure 14:
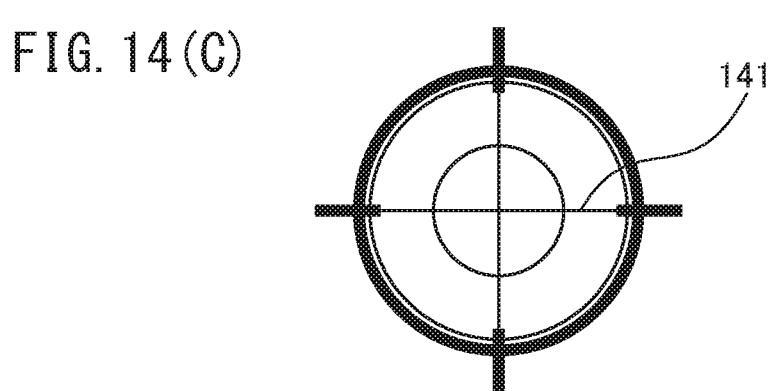

FIGS. 14(A) to 14(C) are diagrams schematically illustrating the configuration of a control device 4 and an example of its usage. The control device 4 is composed of a detector 110, a control terminal 130 and a sighting device 140. The control device 4 is an example of the heart-rate control device, detects pulsation of a hand of a shooter 105 (subject) of target shooting (FIG. 14(A)) or archery (FIG. 14(B)), for example, and outputs color stimuli to the shooter 105 to adjust (decrease) his/her heart rate to a target value, thereby reducing body tremors of the shooter 105.

The detector 110 is an acceleration sensor similar to that of the control device 3, is worn on a hand (e.g., a wrist) of the shooter 105 to detect periodic pulsation of the hand, and outputs the detection signal to the control terminal 130.

The sighting device 140 is a device for the shooter 105 to aim at a target and is attached to a rifle 103 or a bow 104 used by the shooter 105. The sighting device 140 may be of any type as long as it includes, for example, red, blue and green LEDs therein and can display three colors of red, blue and white. FIG. 14(C) shows an example of the line of sight displayed in the sighting device 140. The sighting device 140 is an example of the output unit and displays lines of sight 141 (crossed and circular lines) in red, blue and white as the sympathetic nerve stimulus, the parasympathetic nerve stimulus and the initialization stimulus, respectively, in accordance with the stimulus pattern generated by the control terminal 130. Alternatively, the sighting device 140 may change the color of the display area around the lines of sight 141 (e.g., the regions encircled by the crossed and circular lines, or the region outside the circular line) between red, blue and white.

The control terminal 130 is, for example, a portable device worn by the shooter 105 similarly to that of the control device 3 but may be incorporated in the sighting device 140 or another component unlike the illustrated example. The functions of the control terminal 130 are the same as those of the control device 3. Since a shooter necessarily looks in a sighting device in target shooting and archery, color stimuli through the sighting device are suitable to stimulate the shooter (subject), but the control device 4 may use not only the color stimuli but also the above-described thermal or auditory stimuli. If the heart rate is lowered to extend the intervals of body tremors to approximately 1 second (60 bpm) or longer with the control device 4, the shooter can shoot without being affected by body tremors, and therefore the accuracy of aiming can be improved.

The invention claimed is:

1. A heart-rate control device comprising:
a detector configured to detect heartbeat information of a subject; and
a processor configured to generate, based on the heartbeat information, a stimulus pattern which is a combination of a sympathetic nerve stimulus for stimulating sympathetic nerves and having a first frequency, a parasympathetic nerve stimulus for stimulating parasympathetic nerves and having a second frequency different from the first frequency, and an initialization stimulus for preventing stimulus saturation of the sympathetic nerves or the parasympathetic nerves and having at least a third frequency between the first frequency and the second frequency,
wherein the processor is further configured to: obtain information on a target value relating to a heart rate of the subject,
extract a difference between the target value and a current value relating to the heart rate of the subject, the current value being calculated from the heartbeat information,
generate the stimulus pattern depending on the difference so that the current value approaches the target value, and
output the stimulus pattern, and
wherein the processor is further configured to generate, as the stimulus pattern,
a second stimulus pattern in which the initialization stimulus, the sympathetic nerve stimulus continuing for a first period, the parasympathetic nerve stimulus continuing for a second period, and the initialization stimulus are outputted in sequence, the first period being 1 to 2 seconds, and the second period being 50 to 100 seconds, or
a third stimulus pattern in which the initialization stimulus, the parasympathetic nerve stimulus continuing for the first period, the sympathetic nerve stimulus continuing for the second period, and the initialization stimulus are outputted in sequence, the first period being 1 to 2 seconds, and the second period being 50 to 100 seconds,
wherein as the stimulus pattern, the processor is further configured to generate a first stimulus pattern in which the initialization stimulus is outputted before and after the sympathetic nerve stimulus or the parasympathetic nerve stimulus for a period which is longer than the first period and shorter than the second period.

2. The heart-rate control device according to claim 1, wherein the processor is configured to measure the length of a saturation time using the heartbeat information detected in advance, the saturation time being a period required for the heart rate response of the subject to the sympathetic nerve stimulus or the parasympathetic nerve stimulus to be saturated, and
vary the length of a period corresponding to the sympathetic nerve stimulus or the parasympathetic nerve stimulus in the first, second and third stimulus patterns as a function of the length of the saturation time.

3. The heart-rate control device according to claim 2,
the processor is configured to measure two or more of a base heart rate, a normal heart rate and a post-exercise heart rate of the subject in advance, and
the processor is configured to obtain a value corresponding to a heart rate within a heart rate range of the subject as the information on the target value, the heart rate range being determined by heart rates measured in advance by the processor.

4. The heart-rate control device according to claim 1, further including a light emitter configured to output the sympathetic nerve stimulus, the parasympathetic nerve stimulus, and the initialization stimulus,
wherein the light emitter is configured to emit red light, blue light and white light as the sympathetic nerve stimulus, the parasympathetic nerve stimulus and the initialization stimulus, respectively.

5. The heart-rate control device according to claim 1, further comprising a heating/cooling unit configured to be attached to the skin of the subject, and to be controllable between a first temperature higher than a body temperature and a second temperature lower than the body temperature, the heating/cooling unit being configured to change to the second temperature, the first temperature and the same temperature as the body temperature as the sympathetic nerve stimulus, the parasympathetic nerve stimulus and the initialization stimulus, respectively.

6. The heart-rate control device according to claim 1, further comprising an audio unit configured to play back a piece of music whose tempo is faster than a normal heart rate of the subject, a piece of music whose tempo is slower than the normal heart rate, and a piece of music whose tempo is as fast as the normal heart rate as the sympathetic nerve stimulus, the parasympathetic nerve stimulus and the initialization stimulus, respectively.

7. The heart-rate control device according to claim 1, wherein the processor is configured to obtain, a value indicating speed of the passage of subjective time, the subjective time being time subjectively perceived by the subject, and
extract a difference between the target value and a current value of the speed of the passage of subjective time corresponding to a heart rate of the subject calculated from the heartbeat information.

8. The heart-rate control device according to claim 1, wherein
the processor is configured to obtain, as the target value, a value indicating calorie consumption of the subject, and
extracts a difference between the target value and a current value corresponding to calories that will be consumed if a current heart rate of the subject calculated from the heartbeat information is maintained for a predetermined time.

9. The heart-rate control device according to claim 1, wherein
the detector is an acceleration sensor configured to be worn on a hand of the subject and detect periodic pulsation of the hand synchronized with a heartbeat as the heartbeat information, and
the processor is configured to obtain a value indicating intervals of the pulsation as the target value, and
extract a difference between the target value and a current value of intervals of the pulsation calculated from the heartbeat information.

10. The heart-rate control device according to claim 9, further comprising a sighting device configured to display a line of sight or an area around the line of sight in red, blue and white as the sympathetic nerve stimulus, the parasympathetic nerve stimulus and the initialization stimulus, respectively.

* * * * *